United States Patent [19]

Weiss

[11] 4,108,771

[45] Aug. 22, 1978

[54] ELIMINATION OF ODORS FROM ORGANIC WASTES

[75] Inventor: Josef Weiss, Stockholm, Sweden

[73] Assignees: Weiss & Co.; Kemiska Konsultbyran A.G.; Chemical Consults Corp., Ltd., all of Stockholm, Sweden

[21] Appl. No.: 801,350

[22] Filed: May 27, 1977

Related U.S. Application Data

[63] Continuation of Ser. No. 643,821, Dec. 23, 1975, abandoned, which is a continuation-in-part of Ser. No. 439,879, Feb. 6, 1974, abandoned.

[51] Int. Cl.$^2$ .......................... C02B 1/34; C02C 1/40; C02C 5/04
[52] U.S. Cl. ......................................... 210/50; 21/55; 71/4; 210/52; 210/62; 210/63 R
[58] Field of Search ..................... 21/55, 58, DIG. 3; 71/1, 3, 4, 64 JC; 210/18, 47, 50–53, 59, 62–64; 424/76, 144, 149, 162, 164

[56] References Cited

U.S. PATENT DOCUMENTS

| 2,300,564 | 11/1942 | Godfrey | 210/62 |
| 3,591,515 | 7/1971 | Lovely | 424/76 |
| 3,645,893 | 2/1972 | Rohrer | 210/50 |
| 3,929,637 | 12/1975 | Appleby et al. | 210/63 R |
| 3,966,450 | 6/1976 | O'Neill et al. | 210/63 R |
| 3,989,498 | 11/1976 | Cox | 210/59 |

FOREIGN PATENT DOCUMENTS 4,917 of 1898 United Kingdom ...................... 210/62

OTHER PUBLICATIONS

Cheremisenoff et al., *Industrial Odor Technology Assessment*, Ann Arbor Science, pp. 137 & 138.
Babbitt, *Sewerage and Sewage Treatment*, pp. 446–448, 1958.
Merck Index, 6th Edition, pp. 428 & 433, 1952.

*Primary Examiner*—Thomas G. Wyse
*Assistant Examiner*—Peter A. Hruskoci

[57] ABSTRACT

A method and solution are provided for reducing air-polluting odors emanating from organic waste products produced by metabolic processes and from organic industrial wastes, including effluents, sewage sludges, and the like, the method comprising contacting said wastes with an aqueous acid solution containing a water-soluble oxidizing agent selected from the group consisting of nitrates, chlorates and permanganates of ammonia and alkali metals, and also a precipitating agent selected from the group consisting of water-soluble ferric and ferrous compounds.

3 Claims, No Drawings

ELIMINATION OF ODORS FROM ORGANIC WASTES

This application is a continuation of copending application Ser. No. 643,821, filed Dec. 23, 1975 now abandoned which is a continuation-in-part of U.S. Ser. No. 439,879, filed Feb. 6, 1974 now abandoned.

This invention relates to a novel solution and method for reducing air-polluting odors which emanate from organic waste products, including organic waste products in storage subject to chemical or microbial degradation.

STATE OF THE ART

Methods have been proposed for eliminating odors from organic waste products. However, such methods have not been wholly successful. For example, in the treatment of human wastes, sanitary products, solids or sanitary fluids have been used. Their main objective is to provide a bacteriostatic effect. In general, they act as deodorizers. Actually, they provide an odor-masking effect by employing such aromatics as phenolic compounds, camphor, iso-bornyl acetate, and so forth, the effect being generally temporary.

Different methods have been proposed for reducing the odor of animal waste products in the field where, for example, manure is spread. It has been suggested to aerate animal wastes on a large scale; however, aeration has not been satisfactory due to the low threshold values of certain of the more odorous compounds. The threshold values or minimum identifiable odor (M.I.O.) for mercaptans in mg/l in air range between $10^{-8}$ to $3 \times 10^{-10}$; for dialkylsulfides from about $10^{-8}$ to $2.5 \times 10^{-9}$; for hydrogen sulfide about $10^{-8}$ and for skatole about $1.2 \times 10^{-8}$ mg/l in air.

Another method which has been proposed utilizes the deep-level injection of liquid or liquidified manure into the soil. This method diminishes odors in the surrounding fields but not in the breeding areas. In Sweden, the foregoing was applied to the abatement of odors due to animal wastes on pig breeding farms.

The best results, though still not wholly satisfactory, have been obtained with the use of ammonium persulfate. While unrealistically high amounts of this chemical have been used, they still did not eliminate or reduce the odor entirely. Moreover, the chemical does not attack sulfur-bearing chemicals. The effect of ammonium persulfate has been studied by others, the observations being that while the odor intensity was reduced, it was still not satisfactory.

So far, there has been no satisfactory proposal for abating bad odors from organic industrial wastes, not even from sludges derived from sewage works. For example, an attempt to mask the odor of sewage sludge similarly met with failure.

Many organic wastes are produced daily in large quantities, for example, in large scale animal breeding farms, as effluents from the food industry, waste products from slaughterhouses, sewage and sewage sludge, among others. In these situations, the bad odor is regarded as a public nuisance and as a health hazard, particularly in the situation where waste products are stored for a relatively long period of time, for example, manure and certain soil improving products.

OBJECTS OF THE INVENTION

It is thus the object of the invention to provide an odor removing or odor abating method using chemicals which are not generally harmful to the environment and which do not substantially adversely affect chemical or biological processes usually applied in the further treatment of organic waste products.

Another object of the invention is to provide a method for the ecological recycling of organic waste products without the attendant disadvantages of bad odors.

In accordance with these objects, the present invention is directed to the treatment of waste products, such as organic waste products produced by metabolic processes, including human and animal waste products, as well as to the treatment of organic industrial wastes, effluents, sewage sludges, and the like.

STATEMENT OF THE INVENTION

Stating it broadly, one aspect of the invention is directed to a method of reducing air-polluting odors emanating from waste products, such as organic waste products produced by metabolic processes and from organic industrial wastes including effluents, sewage sludges, and the like, the method comprising, contacting said waste with an aqueous acid solution containing an oxidizing agent selected from the group consisting of water-soluble persulfates, nitrates, chlorates and permanganates of ammonium ion and alkali metals and a precipitating agent selected from the group consisting of water-soluble ferrous and ferric compounds, and then maintaining said contact until said odor has substantially abated.

The use of the foregoing solution results in simultaneous reactions involving the acidification and oxidation of the waste and also in the precipitation of odorless and insoluble sulfides. The chemicals selected are those which have sufficient solubility in cold water and which are substantially harmless to the surrounding environment.

The reactants employed include substantially all acids, the inorganic acids being the most efficient, e.g., sulfuric acid. Acid salts may be employed, such as peroxidisulfates (persulfates), hydrogen sulfates, ferric chloride, and the like. The amount of acid material employed should be such as to provide a pH up to about 6.5 in the mixture, for example, less than a pH of 5.5 or 5. If the pH rises during treatment, more acid may be added. Examples of efficient odor-removing oxidizing agents include soluble persulfates, soluble chlorates, soluble nitrates, soluble permanganates and ferric chloride.

In order to transform such odor-producing chemicals as hydrogen sulfide and organic sulfur compounds into precipitates, water soluble iron salts are used, with ferrous sulfate and ferric chloride being the most efficient.

Each reactant should be present to achieve the results of the invention. For example, neither acidification alone, nor oxidation alone, nor sulfide precipitation alone will adequately remove odors. Successful results are obtained when all three reactants are employed together.

Complete analysis of odorous compounds derived from organic wastes are not available in the literature. The type, as well as the amount of odor-forming compounds, is dependent on the origin of the organic wastes and the conditions and time of storage. The foregoing considerably influence the formation of odorous degradation products.

Empirically, I have observed some chemical properties to be typical of certain types of organic wastes. For example, proteinic wastes, containing relatively more sulfur and nitrogen, develop more odorous compounds and more ammonia. This is particularly true of organic wastes produced by metabolic processes. These wastes contain urea which soon becomes degraded by enzymes to form ammonia, among other by-products.

The chemical demand for certain wastes for the removal of odors is summarized, by way of example, as follows.

Human wastes are treated with about 50 to 100 mg oxygen/Kg of waste (850–950 ml); and animal wastes with about 190 to 205 mg oxygen/liter of waste. As regards organic industrial wastes, average figures are not available as such wastes tend to vary in composition. The chemical demand for sewage normally ranges from about 8 to 10 mg oxygen/l, while sewage sludge (e.g., excess sludge) requires about 17 to 21 mg of oxygen/l (liter).

With regard to the use of iron salts as precipitation agents, for human wastes, about 112 to 180 mg Fe/Kg (850–950 ml) of waste is normally required; for animal wastes, about 150 to 200 mg Fe/l; for sewage, about 30 to 35 mg Fe/l; and for sewage sludges, about 12 to 30 mg Fe/l.

The acid demand expressed in terms of sulfuric acid comprises the following: human wastes, about 3.35 to 3.37 grams/Kg (850–950 ml) of waste; for animal wastes, about 7.9 to 13 grams/l; for sewage, about 0.23 to 0.30 gram/l; and for sewage sludges, about 0.13 to 0.17 gram/l.

The foregoing requirements are met by odor-removing aqueous compositions containing the following amounts of reactants based on mg/gram of solution as applied to certain wastes:

| Type of Waste | SOLUTION COMPOSITION | | |
|---|---|---|---|
| | $mgO_2/g$ | Acid Number mg KOH/g* | mg Fe/g |
| Human Wastes | 8.6–14.0 | 97.2–194.5 | 28–56 |
| Animal Wastes | 56.0–68.0 | 57.0–69.0 | 50–60 |
| Sewage | 40.0–41.0 | 45.0–46.0 | 60 |
| Sewage Sludges | 28.0–35.0 | 45.0–237.0 | 50–70 |

*The acid is determined by the amount of KOH required to neutralize the acid in solution.

In certain cases, further acid may be added to the waste product following treatment with the odor-removing compositions.

Organic waste products containing phosphates, such as in excess sludge from post-precipitation sewage treatment systems, may be treated with solutions containing sufficiently high ferrous or ferric compounds to effect removal of the phosphorous by precipitation as well as removal of the odor. A considerable reduction in sedimentation time is effected using the aforementioned solutions, which is referred to as a secondary effect. This effect is dependent on the pH, optimum sedimentation being achieved at a pH range of about 6 to 6.5, although odor removal is effected at pH's below 5.5 or 5.

The following are examples of waste-treating solution compositions provided by the invention:

EXAMPLE A

| Example A | |
|---|---|
| Water | 568 l |
| $H_2SO_4$ | 120 kg |
| Crystallized Ferrous Sulfate (Heptahydrate) | 250 kg (corresponds to 50.35 g Fe/Kg or 68.9 g Fe/l solution) |
| Sodium Chlorate | 62 kg |

The sulfuric acid is added to water followed by the other ingredients. The final solution has a density at 20° C ($d_{20}$) of 1.370. The total weight of the solution is about 1000 kg, the solution containing 12.0% $H_2SO_4$, 25.0% ferrous sulfate, 6.2% sodium chlorate and the balance about 56.8% water.

EXAMPLE B

| Example B | |
|---|---|
| Water | 345 l |
| 400 Kg solu. containing 280 Kg Ferric Chloride Hexahydrate | 400 kg (corresponds to 58.26 g Fe/Kg or 77.68 g Fe/l solution) |
| Ammonium Nitrate | 85 kg |
| $H_2SO_4$ | 170 kg |

The sulfuric acid is added last to the solution, the solution having a density ($d_{20}$) of 1.333. The total weight of the solution is about 1000 Kg and contains 28% ferric chloride hexahydrate, 8.5% ammonium nitrate, 17% sulfuric acid and the balance essentially 46.5% water.

EXAMPLE C

| Example C | |
|---|---|
| Water | 570 l |
| $H_2SO_4$ | 40 kg |
| Crystallized Ferrous Sulfate (heptahydrate) | 300 kg (60.42 g Fe/kg or 77.4 g Fe/l solution) |
| Sodium Chlorate | 90 kg |

The sulfuric acid is added to the water followed successively by ferrous sulfate and sodium chlorate to produce a solution having a density ($d_{20}$) of 1.282. The weight of the solution is about 1000 Kg and contains 4% $H_2SO_4$, 30% ferrous sulfate, 9% sodium chlorate and the balance about 57% water.

EXAMPLE D

| Example D | |
|---|---|
| Water | 498 l |
| $H_2SO_4$ | 40 kg |
| Crystallized Ferrous Sulfate (heptahydrate) | 357 kg |
| Ammonium chloride | 105 kg |

The sulfuric acid is added to the water followed successively by ferric sulfate and ammonium chlorate to produce a solution having a density ($d_{20}$) of 1.351. The weight of the solution is about 1000 kg and contains 4% sulfuric acid, 35.7% crystallized ferrous sulfate, 10.5% ammonium chloride and the balance about 49.8% water.

EXAMPLE E

| Example E | |
|---|---|
| Water | 335 l |
| $H_2SO_4$ | 170 kg |
| 400 kg solution containing 280 kg of ferric chloride hexahydrate | 400 kg |
| Sodium nitrate | 95 kg |

The sulfuric acid is added last to the solution which has a density ($d_{20}$) of 1.335. The total weight of solution is about 1000 kg and contains 28% ferric chloride hexahydrate, 9.5% sodium nitrate, 17.0% $H_2SO_4$ and the balance about 45.5% water.

It is understood that reference to crystallized ferrous sulfate means the heptahydrate, while reference to ferric chloride means the hexahydrate.

As illustrative of the use of solutions of the foregoing type in removing odors from organic wastes, the following examples are given:

EXAMPLE 1

In the treatment of pig wastes, 3 kg of an odor-removing solution are added per cubic meter of waste, said solution having dissolved therein 25% by weight of crystallized ferrous sulfate, 15% sodium chlorate, 6% sulfuric acid and the balance essentially 54% water. To assure a satisfactory pH in the final mix, a further addition of 3 kg of sulfuric acid is made to the pig wastes. The odor from the pig wastes was immediately abated and, after 1 day, was substantially eliminated.

The soluble reaction products comprised 246 mg of sodium chloride and 4.5 kg of ammonium sulfate per cubic meter.

EXAMPLE 2

Pig wastes are treated with 3.5 kg of an odor-removing solution per cubic meter of waste, the solution containing by weight 30% crystallized ferrous sulfate, 12.3% sodium chlorate, 5.5% sulfuric acid, and the balance essentially 52.2% water. The pH of the wastes is further adjusted by the addition of 2.8 kg of sulfuric acid. The results obtained are the same as for Example 1.

The soluble reaction products included about 239 mg/l of sodium chloride and about 3.9 kg of ammonium sulfate per cubic meter.

EXAMPLE 3

To 1000 kg of human wastes is added 2 kg of an odor-removing solution according to Example B containing 28% ferric chloride hexahydrate, 8.5% ammonium nitrate, 17% sulfuric acid and the balance essentially 46.5% water. The odor was immediately abated. A faint odor of garden compost remained.

The soluble products formed included about 138 mg $NO_2$/Kg (850–950 ml), about 458 mg/kg ammonium sulfate, and about 856 mg/kg of ammonium chloride.

EXAMPLE 4

In the treatment of human wastes in a non-flushed caravan toilet, about 10 grams of solution is proportioned per individual per day, the solution containing by weight 14% ferric chloride, 4.3% ammonium nitrate, 8.5% sulfuric acid and the balance essentially 73.2% water.

The soluble reaction products comprised about 244 mg $NO_2$/Kg, about 800 mg ammonium sulfate/Kg and about 1.5 gram ammonium chloride/Kg.

EXAMPLE 5

Excess sludge from a pre-precipitation sewage treatment is treated by adding 0.75 kg of solution per cubic meter thereof according to the composition of Example A containing about 26.7% of crystallized ferrous sulfate, about 6.6% sodium chlorate, about 12.7% $H_2SO_4$ and the balance essentially 54% water. The repulsive odor was immediately abated to a faint odor of mould. This odor lasted to at least the dewatering and concentration steps. The latter steps were facilitated due to a marked decrease in sedimentation time and increase in the final solids content, especially at a pH in the range of about 6 to 6.5 due to flocculation. The foregoing operation was carried out continuously for 6 weeks at a flow rate of 35 to 45 liters of excess sludge per second.

The soluble reaction products included about 25 mg/l of sodium chloride and about 120 mg/l of ammonium sulfate (87 mg/l $SO_4$).

EXAMPLE 6

About 0.5 Kg of an odor-removing solution corresponding to Example C is added per cubic meter of excess sludge from a pre-precipitation sewage treatment system, the solution containing 30% dissolved crystallized ferrous sulfate, 9% sodium chlorate, 4% sulfuric acid and essentially 57% water. The pH was adjusted on the acid side by adding 80 grams of sulfuric acid per cubic meter of waste. The results obtained were similar to Example 5, that is to say, the sedimentation rate was considerably increased.

The soluble reaction products include about 25 mg/l of sodium chloride and about 126 mg/l of ammonium sulfate (92 mg/l $SO_4$).

EXAMPLE 7

Excess sludge from a post-precipitation sewage treatment system is treated by adding 0.5 Kg of odor-removing solution per cubic meter of waste, the solution comprising 35% of dissolved crystallized ferrous sulfate, 7.6% sodium chlorate, 4% sulfuric acid and the balance essentially 53.4% water. Following the addition of the solution, the pH was further adjusted by the addition of 90 grams of sulfuric acid per cubic meter of waste. The results obtained corresponded to those obtained in Examples 5 and 6.

The soluble reaction products included about 21 mg/l of sodium chloride, and about 138 mg/l of ammonium sulfate (101 mg/l $SO_4$)

EXAMPLE 8

Sewage previously treated mechanically to remove coarse solids is subjected to the method of the invention by adding 0.4 Kg of odor-removing solution per cubic meter of said sewage. The solution contained by weight 30% dissolved crystallized ferrous sulfate, 9% sodium chlorate, 4% sulfuric acid and essentially 57% water. Following addition of the solution, the pH of the mixture was adjusted by a further addition of 195 grams per cubic meter of sulfuric acid. The odor was immediately eliminated and spontaneous flocculation and sedimentation occurred. About 90% of the original phosphorus was removed.

The soluble reaction products included about 19.6 mg/l of sodium chloride and about 267 mg/l of ammonium sulfate (194 mg/l SO$_4$).

As indicated hereinbefore, the solution of the invention has the additional advantage of reducing the sedimentation time in crude sludges. This secondary effect which is achieved at a pH of about 6 to 6.5 is due to flocculation which decreases the amount of polyelectrolytes required for this purpose which are quite expensive. Flocculation helps in dewatering sludges using presses, vacuum presses, centrifuges and the like.

In domestic sewage, organic pollutants generally dominate. An example of domestic sewage is one containing 200 grams solid per cubic meter with organics making up 60% by weight of the solids.

Sludge dewatered by pressing may contain about 10 to 15% solids and by centrifuging about 15 to 20% by weight of solids, the solids containing anywhere from about 50 to 80% by weight of organics. Digested sludges after decantation may have a solids content of about 8% with 50 to 60% of the solids as organics.

Sludges treated in accordance with the invention may range in solids content from about 0.5% by weight upwards to 4% for crude sludges or to as high as 5 or 6% for thickened sludges or even as high as 10 to 20% for dewatered sludges. Most sewage sludges as well as industrial effuents are more or less opaque to the eye, even with solids contents of 0.5% or lower, the sludges or effluents being quite dark or black and having a disgusting smell due to dissolved odor-producing substances.

The invention is particularly applicable to the treatment of crude or thickened sludges in which the odor removal is carried out while taking advantage of the flocculation propensity of the solution at a pH above 5.5, for example, at about 6 to 6.5.

As will be evident from the foregoing examples, the composition of the odor-removing solution may vary over a relatively broad range. Thus, the solution may comprise by weight about 3 to 25% sulfuric acid, about 3 to 20% of an oxidizing agent from the group consisting of water soluble persulfates, nitrates, chlorates and permanganates of ammonia ion and alkali metals, e.g. sodium chlorate and ammonium nitrate, about 10 to 40% of an iron salt from the group including hydrates of ferrous sulfate and ferric chloride, and the balance at least about 40% water.

Although the present invention has been described in conjunction with preferred embodiments, it is to be understood that modifications and variations may be resorted to without departing from the spirit and scope of the invention as those skilled in the art will readily understand. Such modifications and variations are considered to be within the purview and scope of the invention and the appended claims.

What is claimed is:

1. A method of reducing air-polluting odors including odor-producing compounds of organic sulfur compounds and ammonia emanating from a solids-containing waste product selected from the group consisting of organic waste products produced by metabolic processes including animal and human wastes, organic industrial wastes and sewage sludges which comprises, forming a mixture of said odorous solids-containing waste product with an effective odor-abating amount of an aqueous acid solution containing by weight about 3 to 25% sulfuric acid, about 3 to 20% of an oxidizing agent selected from the group consisting of water soluble persulfates, nitrates, chlorates and permanganates of ammonium ion and alkali metals sufficient to oxidize said solids-containing waste product and substantially reduce the odor thereof and about 10 to 40% of a sulfur precipitating agent selected from the group consisting of water-soluble ferrous and ferric compounds sufficient to form precipitates with sulfur contained in said odor-producing compounds, and maintaining said mixture at a pH not exceeding 6.5 until said odor has been substantially abated.

2. The method of claim 1, wherein the precipitating agent is from the group of ferrous sulfate heptahydrate and ferric chloride hexahydrate, and wherein the pH of said mixture is below 5.

3. The method of claim 1, wherein said oxidizing agent is from the group sodium chlorate and ammonium nitrate.

* * * * *